United States Patent
Sakamoto et al.

(10) Patent No.: US 9,075,073 B1
(45) Date of Patent: Jul. 7, 2015

(54) COMPOUND-ANALYZING METHOD, COMPOUND ANALYZER AND COMPUTER READABLE MEDIUM RECORDING A COMPOUND-ANALYZING PROGRAM

(71) Applicant: SHIMADZU CORPORATION, Kyoto-shi, Kyoto (JP)

(72) Inventors: Yuki Sakamoto, Kyoto (JP); Haruhiko Miyagawa, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 0 days.

(21) Appl. No.: 14/624,783

(22) Filed: Feb. 18, 2015

(30) Foreign Application Priority Data

Mar. 26, 2014 (JP) ................. 2014-063550

(51) Int. Cl.
- B01D 59/44 (2006.01)
- G01N 30/02 (2006.01)
- H01J 49/00 (2006.01)
- G01N 30/72 (2006.01)
- H01J 49/26 (2006.01)

(52) U.S. Cl.
CPC ........ G01N 30/7206 (2013.01); H01J 49/0081 (2013.01); H01J 49/26 (2013.01); G01N 30/7233 (2013.01)

(58) Field of Classification Search
CPC .................. C12Q 2565/518; C12Q 2565/627; G01N 33/6803; G01N 33/6848; G01N 33/6851; G01N 33/52
USPC .............. 250/288, 281, 282; 435/147; 506/12
See application file for complete search history.

(56) References Cited

U.S. PATENT DOCUMENTS

| | | | | |
|---|---|---|---|---|
| 2006/0123883 | A1* | 6/2006 | Miyagawa | 73/23.37 |
| 2012/0252052 | A1* | 10/2012 | Matsukawa et al. | 435/29 |
| 2015/0094233 | A1* | 4/2015 | Matsukawa et al. | 506/12 |

OTHER PUBLICATIONS

Hitoshi Tsuchihashi, "'GC/MS-hou Yakudokubutsu Deetabeesu' Wo Riyou-shita Kessei-chuu Kouseishin-yaku No Jidou Doutei to Hanteiryou Bunseki (Automated Identification and Semi-Quantitative Analysis of Serum Psychotropic Drug Using 'Drugs and Poisons Database for GC/MS Method')", a document published in SHIMADZU GC/MS Technical Report No. 6 on Shimadzu Corporation's website.

"Yakuji-hou Dai 2 Jou Dai 14 Kou Ni Kitei-suru Shitei Yakubutsu Oyobi Dou-hou Dai 76 Jou No. 4 Ni Kitei-suru Iryou-tou No Youto Wo Sadameru Shourei No. Ichibu Kaisei Ni Tsuite (Sikou Tsuuchi) (Partial Amendment to Ministry Ordinance Specifying the Scheduled Drugs under Article 2(14) of the Pharmaceutical Affairs Act as well as the Medical and Other Uses under Article 76-4 of the Same Act (Notice of Enforcement))", a document published on the website of the Ministry of Health, Labor and Welfare.

* cited by examiner

Primary Examiner — Nikita Wells
(74) Attorney, Agent, or Firm — Sughrue Mion, PLLC

(57) ABSTRACT

For the detection and structural analysis of cathinone-based compounds subject to comprehensive regulation, three MS/MS measurements are repeated for a target sample: an MRM measurement; a product-ion scan measurement; and a product-ion scan measurement. Based on the positional coincidence of a peak on chromatograms obtained by the three measurements, non-cathinone-based compounds are excluded. From the MRM transition and the product-ion spectrum pattern, the kinds of functional groups are estimated and the structure of the cathinone-based compound is estimated.

4 Claims, 14 Drawing Sheets

Fig. 3
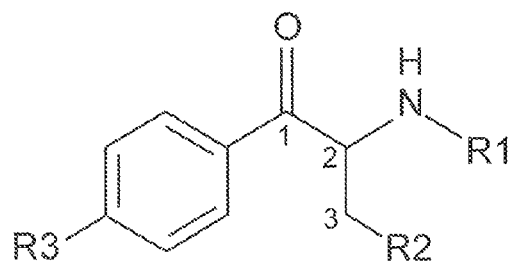
Fig. 4
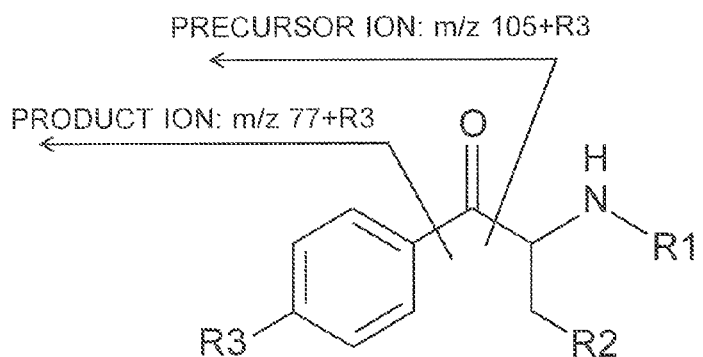
Fig. 5
| MRM TRANSITION | FUNCTIONAL GROUP |
|---|---|
| 105.0 > 77.0 | R3 : HYDROGEN |
| 119.0 > 91.0 | R3 : METHYL |
| 133.0 > 105.0 | R3 : ETHYL |
| 135.0 > 107.0 | R3 : METHOXY |
| 123.0 > 95.0 | R3 : FLUORINE |
| 139.0 > 111.0 | R3 : CHLORINE |
| 183.0 > 155.0 | R3 : BROMINE |
| 231.0 > 203.0 | R3 : IODINE |
| 149.0 > 121.0 | R3 : METHYLENEDIOXY |

Fig. 6A   MRM TRANSITION: m/z: 105>77 (R3:H)
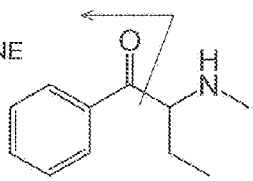
BUPHEDRONE
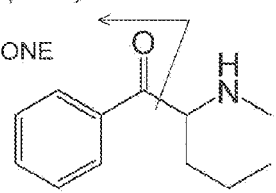
PENTEDRONE
Fig. 6B   MRM TRANSITION: m/z: 119>91 (R3:CH3)
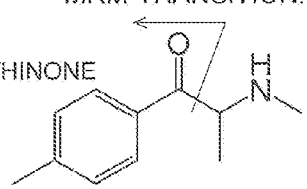
4-METHYL METHCATHINONE
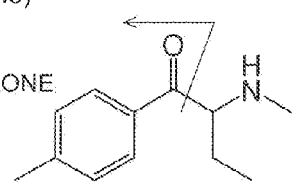
4-METHYL BUPHEDRONE
Fig. 6C   MRM TRANSITION: m/z: 135>107 (R3:OCH3)
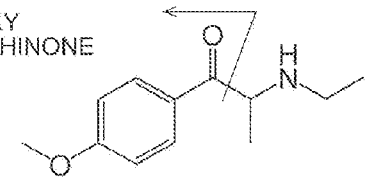
4-METHOXY ETHCATHINONE
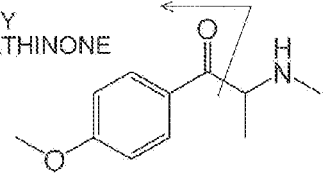
4-METHOXY METHCATHINONE

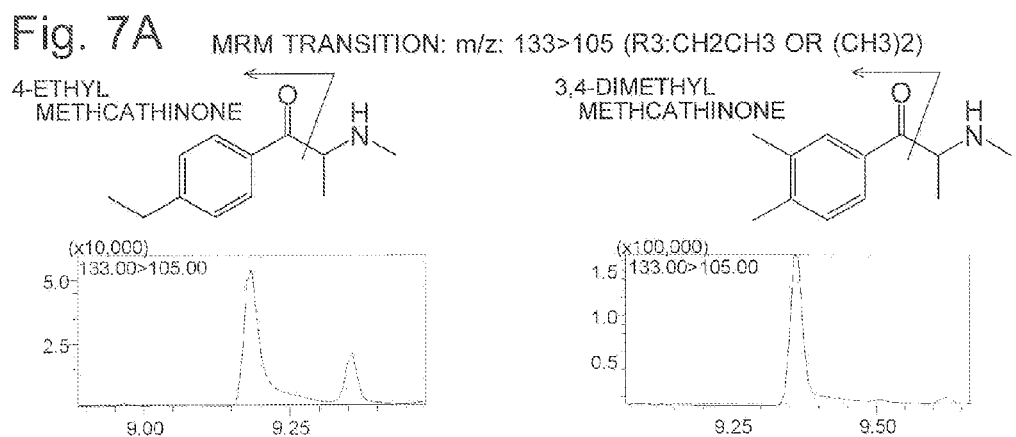
Fig. 7A  MRM TRANSITION: m/z: 133>105 (R3:CH2CH3 OR (CH3)2)
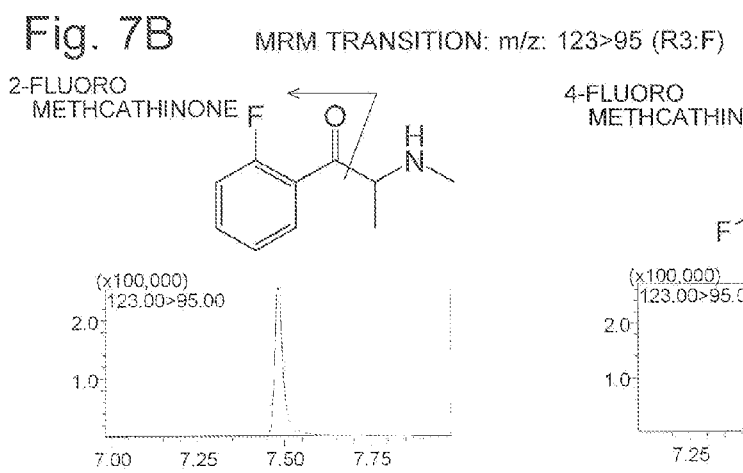
Fig. 7B  MRM TRANSITION: m/z: 123>95 (R3:F)
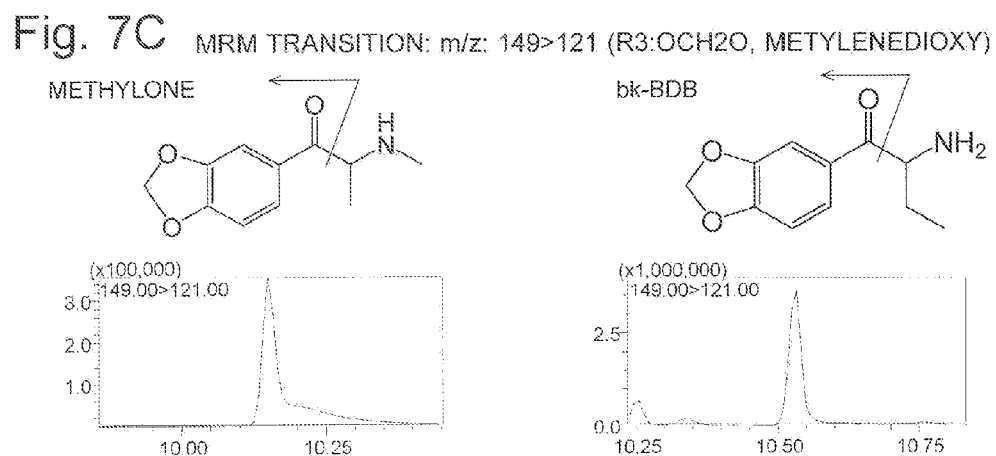
Fig. 7C  MRM TRANSITION: m/z: 149>121 (R3:OCH2O, METYLENEDIOXY)

Fig. 8
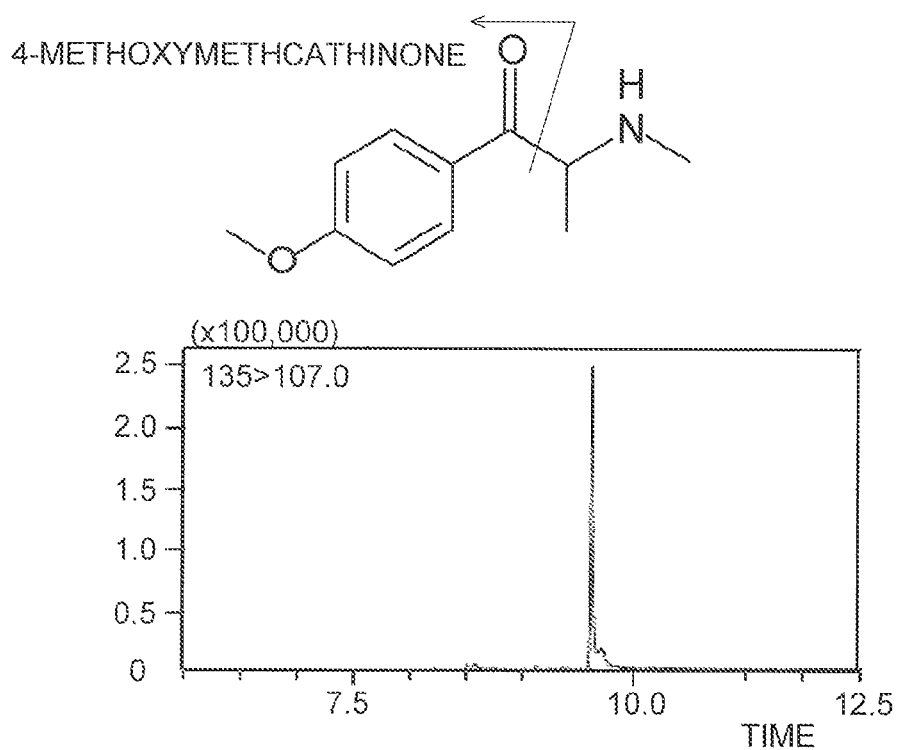
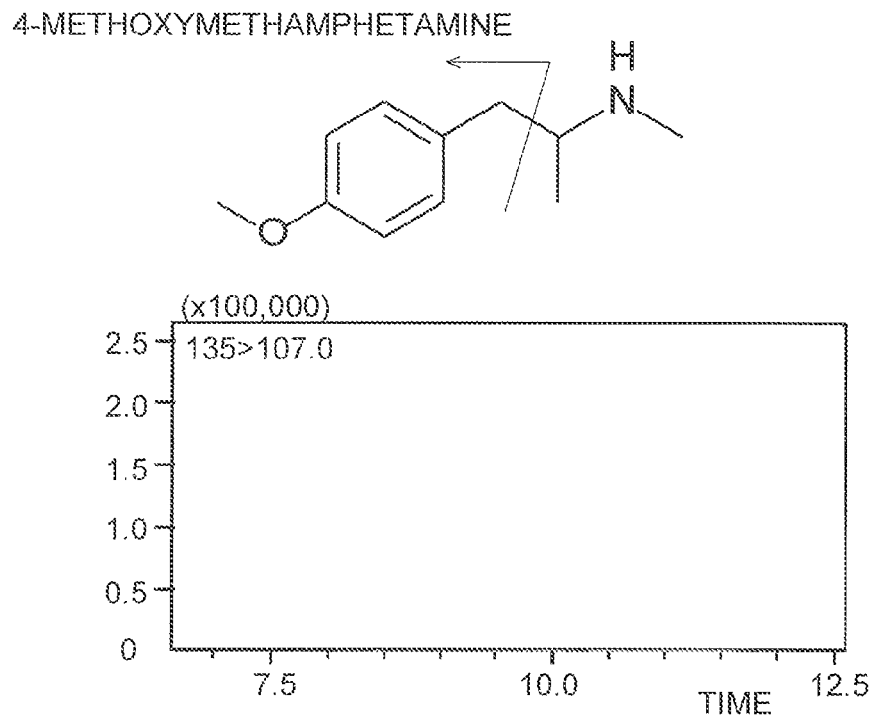

PRECURSOR ION: m/z 42+R1+R2

| PRECURSOR m/z | R1 FUNCTIONAL GROUP | R2 FUNCTIONAL GROUP |
|---|---|---|
| 44 | H | H |
| 58 | CH3 | H |
|    | H | CH3 |
| 72 | H | C2H5 |
|    | CH3 | CH3 |
|    | CH2H5 | H |
|    | (CH3)2 | H |
| 86 | CH3 | CH2CH3 |
|    | CH2CH3 | CH3 |
|    | (CH3)2 | CH3 |
|    | (CH2CH3)CH3 | H |
| 100 | CH2CH3 | CH2CH3 |
|     | (CH3)2 | CH2CH3 |
|     | (CH2CH3)CH3 | CH3 |
|     | (CH2CH3)2 | H |
| 114 | (CH2CH3)2 | CH3 |
|     | (CH2CH3)CH3 | CH2CH3 |
| 128 | (CH2CH3)2 | CH2CH3 |
| 98  | C5H8 | H |
| 112 | C5H8 | CH3 |
| 126 | C5H8 | CH2CH3 |

Fig. 11A PRECURSOR m/z: 44
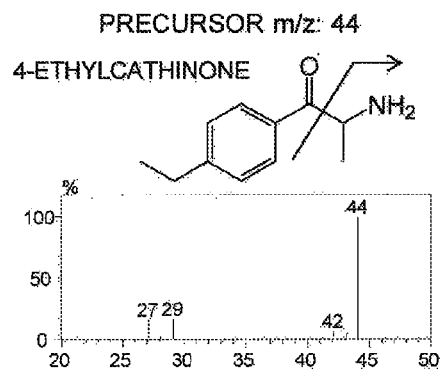
Fig. 11B PRECURSOR m/z: 58
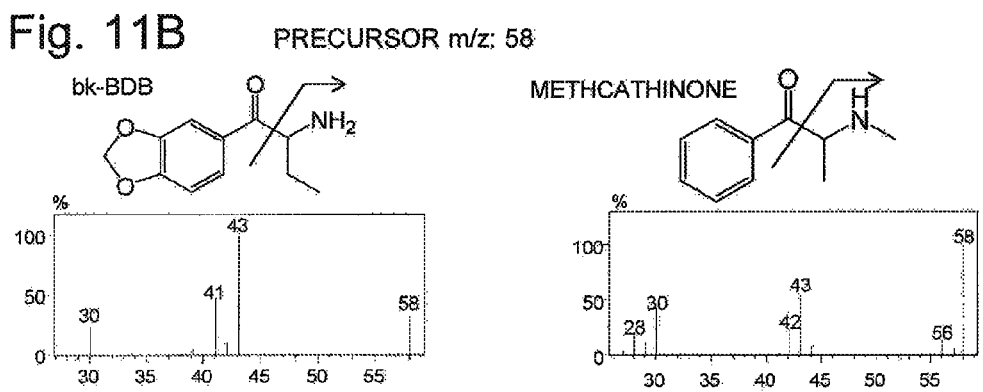
Fig. 11C PRECURSOR m/z: 72
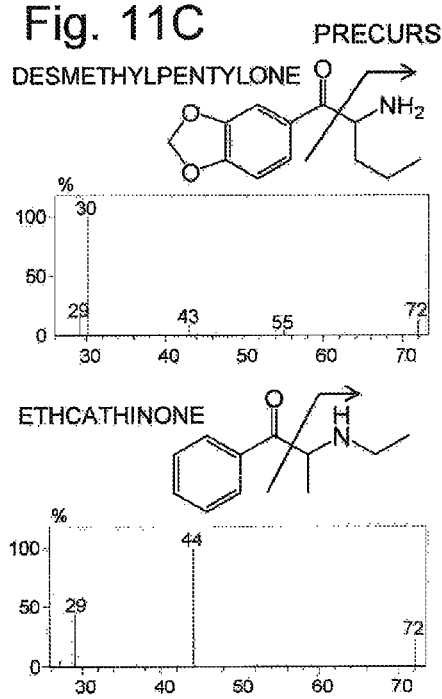
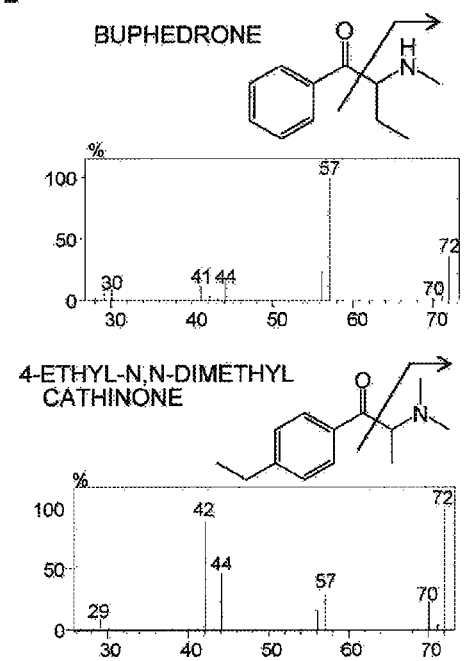

Fig. 12A  PRECURSOR m/z: 86
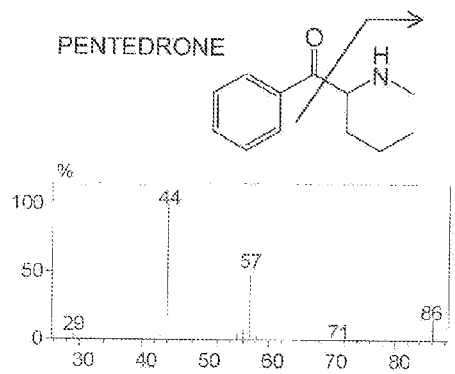
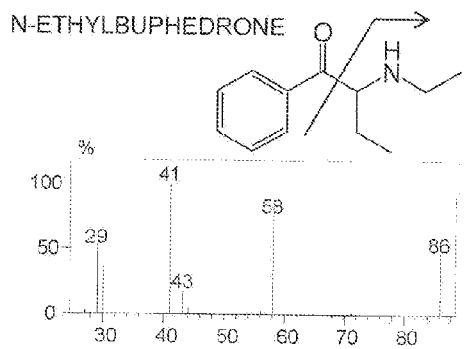
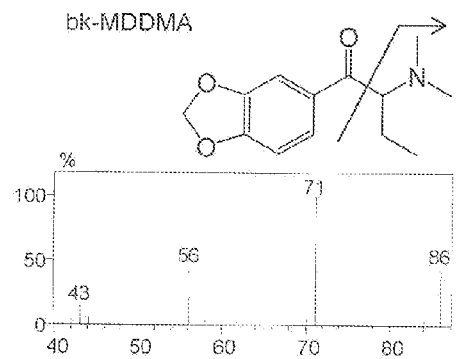
Fig. 12B  PRECURSOR m/z: 100
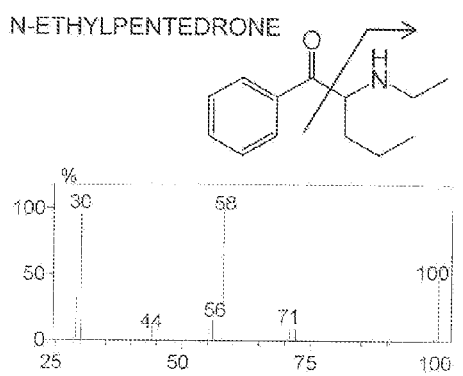
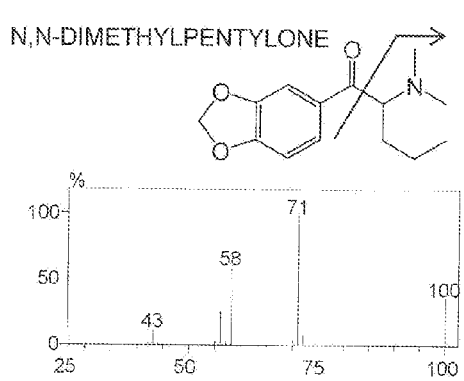

Fig. 13A  PRECURSOR m/z: 98
α-PPP
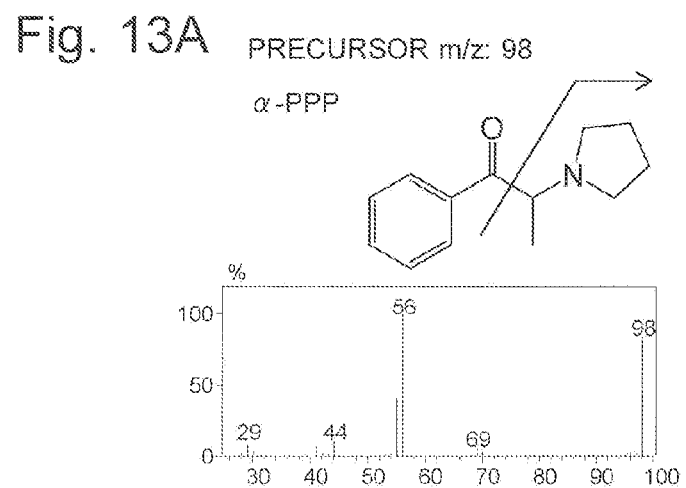
Fig. 13B  PRECURSOR m/z: 112
α-PBP
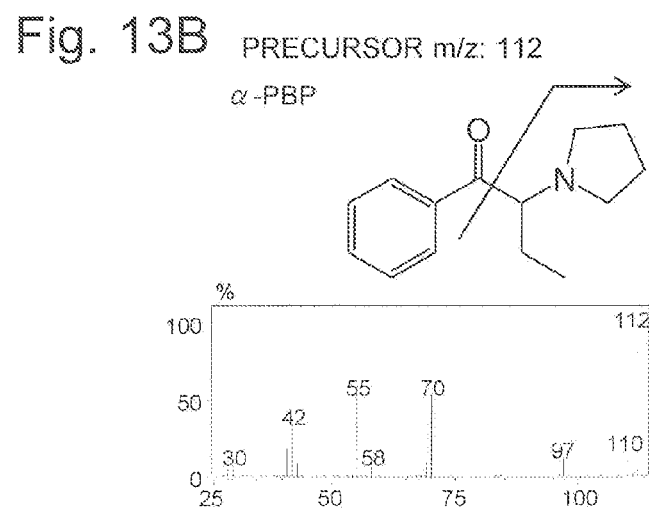
Fig. 13C  PRECURSOR m/z: 126
α-PVP
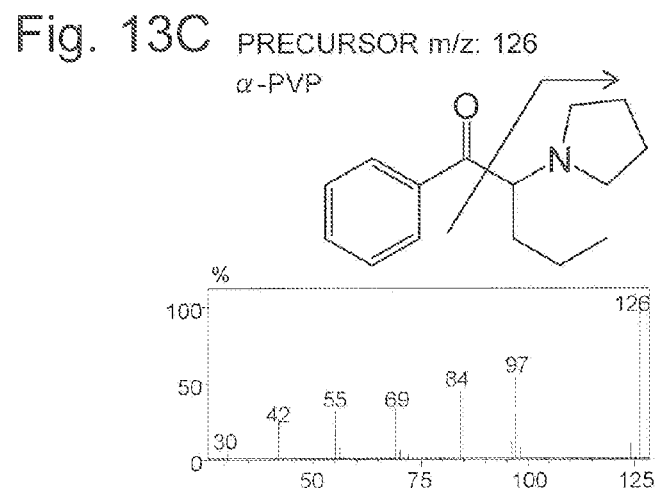

PRECURSOR ION: m/z 105+R3

| PRECURSOR m/z | R3 FUNCTIONAL GROUP |
|---|---|
| 105 | H |
| 119 | CH3 |
| 123 | F |
| 133 | C2CH3 OR (CH3)2 |
| 135 | OCH3 |
| 139 | Cl |
| 149 | OCH2O (METHYLENEDIOXY) |
| 183 | Br |
| 231 | I |

Fig. 16A  PRECURSOR m/z: 105 (R3:H)
BUPHEDRONE
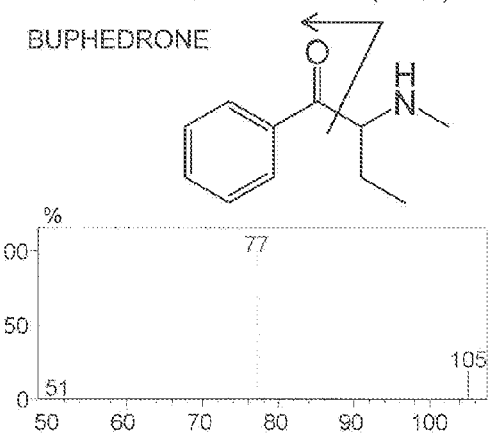
Fig. 16B  PRECURSOR m/z: 119 (R3:CH3)
4-METHYLMETHCATHINONE
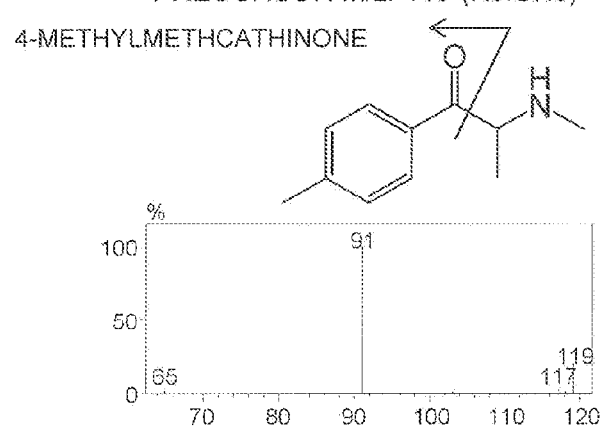
Fig. 16C  PRECURSOR m/z: 135 (R3:OCH3)
4-METHOXYETHCATHINONE
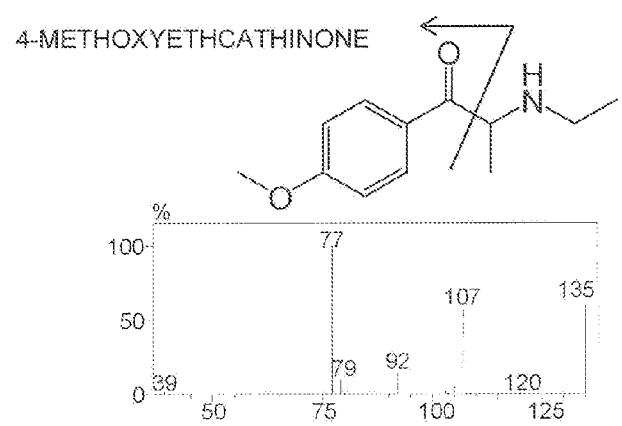

Fig. 17
PRECURSOR m/z: 133 (R3:CH2H3 OR (CH3)2)
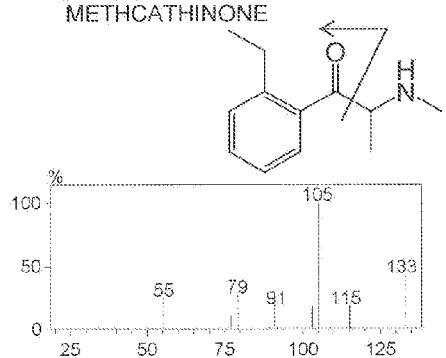
2-ETHYL METHCATHINONE
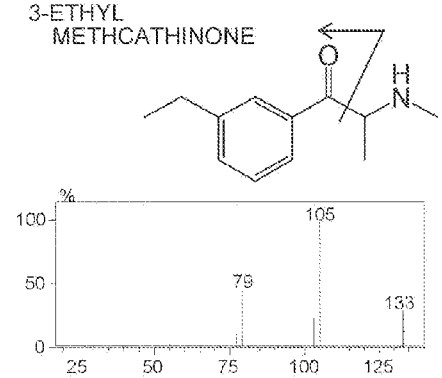
3-ETHYL METHCATHINONE
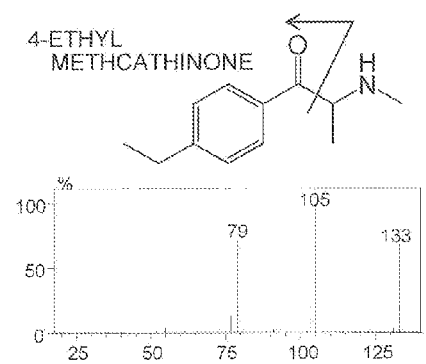
4-ETHYL METHCATHINONE
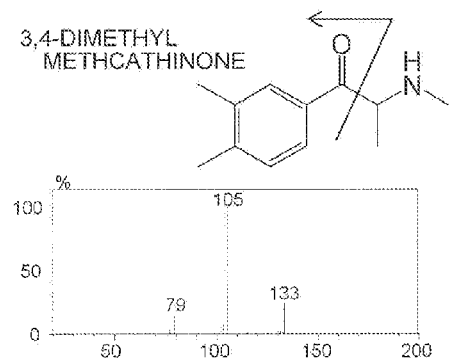
3,4-DIMETHYL METHCATHINONE Fig. 18A
PRECURSOR m/z: 123 (R3:F)
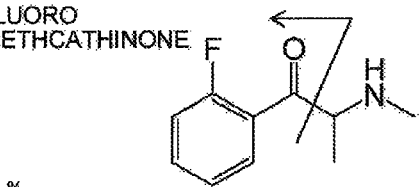
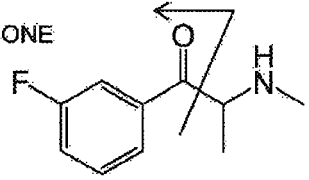
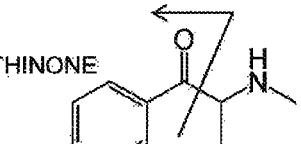
Fig. 18B  PRECURSOR m/z: 149 (R3:OCH2O)
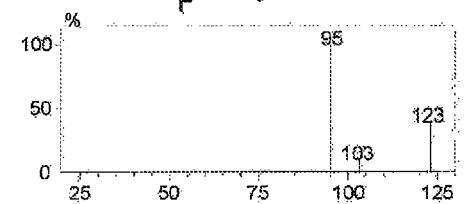

COMPOUND-ANALYZING METHOD, COMPOUND ANALYZER AND COMPUTER READABLE MEDIUM RECORDING A COMPOUND-ANALYZING PROGRAM

TECHNICAL FIELD

The present invention relates to a compound-analyzing method, a compound analyzer, and a computer-readable medium recording a compound-analyzing program for estimating the structure of a specific compound by a gas chromatograph mass spectrometer using a mass spectrometer capable of an MS/MS measurement, or by a system with which a result similar to an MS/MS measurement by the aforementioned type of gas chromatograph mass spectrometer can be obtained, such as a liquid chromatograph mass spectrometer capable of an MS/MS measurement and an in-source collision-induced dissociation (CID) or a liquid chromatograph ion-trap mass spectrometer capable of an $MS^n$ measurement.

BACKGROUND ART

The spread of illicit drugs, such as narcotics and stimulants, has been a global problem. In many countries including Japan, illicit drugs having effects similar to stimulants or cannabis (such drugs are generally called "dangerous drugs" in Japan) are regulated individually (i.e. for each compound). In recent years, a wide variety of analogue compounds produced by partially altering the backbone chemical structures of existing drugs or by replacing their functional groups with different ones have been circulating one after another, making it difficult to regulate every individual compound. To deal with such a situation, a so-called comprehensive regulation, which is aimed at regulating compounds by their main skeletons rather than regulating individual illicit drugs, has been put into effect in some countries and regions, such as Japan, the UK and some of the states in the United States.

In general, identification of such illicit drugs or poisons has been performed using a gas chromatograph mass spectrometer (GC-MS) or liquid chromatograph mass spectrometer (LC-MS). Specifically, this is normally achieved as follows: A mass spectrum obtained by a measurement of a target sample using a GC-MS or LC-MS is compared with mass spectra obtained by measurements of known kinds of standard samples or mass spectra contained in a commonly available database, so as to search for a compound having a spectrum pattern identical or similar to that of the obtained mass spectrum and thereby identify the compound detected in the target sample (for example, see Non Patent Literature 1).

However, in many cases, it is difficult to obtain a standard sample for a newly circulated illicit drug produced by the aforementioned partial alteration of a chemical structure. Furthermore, mass spectra corresponding to such drugs are not contained in any existing databases, while at the same time it is not easy to create a database which completely contains mass spectra of a large number of compounds subject to the comprehensive regulation. Therefore, it is considerably difficult to identify all the illicit drugs subject to the comprehensive regulation or estimate their structures, by the aforementioned conventional method which uses a GC-MS or LC-MS.

For example, the comprehensive schedule prepared under the Pharmaceutical Affairs Act in Japan (see Non Patent Literature 2) contains a list of compounds which have the main skeleton consisting of 2-amino-1-phenyl-propane-1-one (commonly called "cathinone") as being subject to the comprehensive regulation. The list shows 495 kinds of cathinone-based compounds which differ from each other in the kinds of functional groups bonded to three sites on this main skeleton. FIG. 3 shows the chemical structure of cathinone-based compounds. As will be detailed later, R1 is either hydrogen (H) or one of six kinds of substituent groups, thus providing seven choices. R2 is either occupied by one of two kinds of substituent groups or unoccupied by any substituent group, thus providing three choices. R3 is either occupied by one of eight kinds of substituent groups (with a total of 23 patterns having different bonding sites) or unoccupied by any substituent group, thus providing 24 choices.

For such a large number of cathinone-based compounds, the conventional method of identifying compounds by the pattern matching of mass spectra cannot be used to identify the compounds or estimate their structures unless those compounds are individually registered in a database.

In GC-MS, an electron ionization (EI) method is widely used as the ionization method. However, when the EI method is used for a cathinone-based compound, there will be almost no molecular ion detectable on the obtained mass spectrum. The amount of fragment information will also be small, since the thereby detected fragment ions are only the ions produced by α-fragmentation of amine. Therefore, even if the target compound to be identified is registered in a database, it is difficult to accurately distinguish this target compound from phenethylamine-based compounds, whose mass-spectrum patterns are similar to those of the cathinone-based compounds. Such a high degree of similarity to the phenethylamine-based compounds makes it even more difficult to identify the cathinone-based compounds.

To deal with such a problem, an attempt of structural estimation has been made in which the result of an analysis using a GC-MS is combined with high-precision mass information obtained using a nuclear magnetic resonance (NMR) apparatus, liquid chromatograph time-of-flight mass spectrometer (LC-TOFMS) or similar device. However, this method requires preparing a plurality of devices, each of which is expensive. Furthermore, a highly experienced operator is needed to conduct measurements and analyze data.

CITATION LIST

Non Patent Literature

Non Patent Literature 1: Hitoshi Tsuchihashi, "'GC/MS-hou Yakudokubutsu Deetabeesu' Wo Riyou-shita Kessei-chuu Kouseishin-yaku No Jidou Doutei To Han-teiryou Bunseki (Automated Identification and Semi-Quantitative Analysis of Serum Psychotropic Drug Using 'Drugs and Poisons Database for GC/MS Method')", a document published in SHIMADZU GC/MS Technical Report No. 6 on Shimadzu Corporation's website.

Non Patent Literature 2: "Yakuji-hou Dai 2 Jou Dai 14 Kou Ni Kitei-suru shitei Yakubutsu Oyobi Dou-hou Dai 76 Jou No 4 Ni Kitei-suru Iryou-tou No Youto Wo Sadameru Shourei No Ichibu Kaisei Ni Tsuite (Sikou Tsuuchi) (Partial Amendment to Ministry Ordinance Specifying the Scheduled Drugs under Article 2(14) of the Pharmaceutical Affairs Act as well as the Medical and Other Uses under Article 76-4 of the Same Act (Notice of Enforcement))", a document published on the website of the Ministry of Health, Labor and Welfare.

SUMMARY OF INVENTION

Technical Problem

The present invention has been developed to solve the previously described problem. Its objective is to provide a compound-analyzing method, a compound analyzer and a computer-readable medium recording a compound-analyzing program by which a cathinone-based compound which has no standard sample or has its mass spectra or similar information contained in no database can be assuredly detected and its chemical structure can be estimated with high accuracy, using apparatuses which are easy to obtain and comparatively inexpensive.

Solution to Problem

The present invention aimed at solving the previously described problem provides a compound-analyzing method for detecting a cathinone-based compound having cathinone as a basic skeleton and for estimating the structure of the cathinone-based compound, using a chromatograph mass spectrometer capable of an MS/MS measurement, the compound-analyzing method including:
  a) a measurement execution step, in which a sample which contains or possibly contains a compound which is an analysis target is separated into components by a chromatograph and two or three kinds of MS/MS measurements are repeatedly performed on the sample, the two or three kinds of measurements including:
    a1) one or both of the following two kinds of measurements: an MRM measurement, in which a benzoyl part produced by α-fragmentation during an ionization process is selected as a precursor ion, a benzene part produced by dissociation of a carbonyl group from the benzoyl part is selected as a product ion, and a plurality of MRM transitions corresponding to possible values of the mass of a third functional group bonded to a benzene ring are specified as measurement conditions; and a second product-ion scan measurement performed for a benzoyl part produced by α-fragmentation during an ionization process, in which each of a plurality of kinds of benzoyl parts corresponding to the possible mass values of the third functional group is selected as a precursor ion; and
    a2) a first product-ion scan measurement performed for an amine part produced by α-cleavage during an ionization process, in which each of a plurality of kinds of amine parts corresponding to possible values of the total mass of a first functional group and a second functional group respectively bonded to different sites on the amine part is selected as a precursor ion;
  b) a compound presence checking step, in which the presence of a cathinone-based compound is judged by determining whether or not a common peak exists at the same retention time on chromatograms respectively corresponding to the two or three kinds of measurements, the chromatograms being created based on data respectively obtained by the MRM measurement and/or the second product-ion scan measurement as well as the first product-ion scan measurement; and
  c) a structure estimation step, in which the kind of the third functional group is estimated based on the data obtained by the MRM measurement and/or the second product-ion scan measurement, the kinds of the first functional group and the second functional group are estimated based on the data obtained by the first product-ion scan measurement, and the results of these estimations are combined to estimate the structure of a cathinone-based compound whose presence is confirmed in the compound presence checking step.

The present invention aimed at solving the previously described problem also provides a compound analyzer for realizing the previously described compound-analyzing method according to the present invention. The compound analyzer includes a chromatograph mass spectrometer capable of an MS/MS measurement and is configured to detect a cathinone-based compound having cathinone as a basic skeleton and to estimate the structure of the cathinone-based compound, the compound analyzer further including:
  a) an analysis controller for making the chromatograph mass spectrometer operate so as to separate a sample which contains or possibly contains a compound which is an analysis target into compounds by a chromatograph and to repeatedly perform two or three kinds of MS/MS measurements on the sample, the two or three kinds of MS/MS measurements including:
    a1) one or both of the following two kinds of measurements: an MRM measurement, in which a benzoyl part produced by α-cleavage during an ionization process is selected as a precursor ion, a benzene part produced by dissociation of a carbonyl group from the benzoyl part is selected as a product ion, and a plurality of MRM transitions corresponding to possible values of the mass of a third functional group bonded to a benzene ring are specified as measurement conditions; and a second product-ion scan measurement performed for a benzoyl part produced by α-cleavage during an ionization process, in which each of a plurality of kinds of benzoyl parts corresponding to the possible mass values of the third functional group is selected as a precursor ion; and
    a2) a first product-ion scan measurement performed for an amine part produced by α-cleavage during an ionization process, in which each of a plurality of kinds of amine parts corresponding to possible values of the total mass of a first functional group and a second functional group respectively bonded to different sites on the amine part is selected as a precursor ion;
  b) a compound presence checker for collecting data respectively obtained by the MRM measurement and/or the second product-ion scan measurement as well as the first product-ion scan measurement, for creating chromatograms corresponding to the two or three kinds of MS/MS measurements based on the data, and for judging the presence of a cathinone-based compound by determining whether or not a common peak exists at the same retention time on the chromatograms; and
  c) a structure estimator for estimating the kind of the third functional group based on the data obtained by the MRM measurement and/or the second product-ion scan measurement, for estimating the kinds of the first functional group and the second functional group based on the data obtained by the first product-ion scan measurement, and for combining the results of these estimations to estimate the structure of a cathinone-based compound whose presence is confirmed by the compound presence checker.

The present invention aimed at solving the previously described problem also provides a computer-readable medium recording a computer program for realizing the previously-described compound-analyzing method according to the present invention, the compound-analyzing program being configured to be executed on a computer so as to control an operation of a chromatograph mass spectrometer capable of an MS/MS measurement as well as to collect and process data obtained by the chromatograph mass spectrometer in order to detect a cathinone-based compound having cathinone as a basic skeleton and estimate the structure of the cathinone-based compound, the compound-analyzing program including:
  a) an analysis control functional part for making the chromatograph mass spectrometer operate so as to separate a sample which contains or possibly contains a compound which is an analysis target into compounds by a chromatograph and to repeatedly perform two or three kinds of MS/MS measurements on the sample, the two or three kinds of MS/MS measurements including:

a1) one or both of the following two kinds of measurements: an MRM measurement, in which a benzoyl part produced by α-cleavage during an ionization process is selected as a precursor ion, a benzene part produced by dissociation of a carbonyl group from the benzoyl part is selected as a product ion, and a plurality of MRM transitions corresponding to possible values of the mass of a third functional group bonded to a benzene ring are specified as measurement conditions; and a second product-ion scan measurement performed for a benzoyl part produced by α-cleavage during an ionization process, in which each of a plurality of kinds of benzoyl parts corresponding to the possible mass values of the third functional group is selected as a precursor ion; and a2) a first product-ion scan measurement performed for an amine part produced by α-cleavage during an ionization process, in which each of a plurality of kinds of amine parts corresponding to possible values of the total mass of a first functional group and a second functional group respectively bonded to different sites on the amine part is selected as a precursor ion;

b) a compound presence checking functional part for creating chromatograms corresponding to the two or three kinds of MS/MS measurements based on data respectively obtained by the MRM measurement and/or the second product-ion scan measurement as well as the first product-ion scan measurement, and for judging the presence of a cathinone-based compound by determining whether or not a common peak exists at the same retention time on the chromatograms; and c) a structure estimation functional part for estimating the kind of the third functional group based on the data obtained by the MRM measurement and/or the second product-ion scan measurement, for estimating the kinds of the first functional group and the second functional group based on the data obtained by the first product-ion scan measurement, and for combining the results of these estimations to estimate the structure of a cathinone-based compound whose presence is confirmed by a process performed by the compound presence checking functional part.

In the compound-analyzing method, the compound analyzer and the computer-readable medium recording a compound-analyzing program according to the present invention, the chromatograph mass spectrometer does not only need to be capable of an MS/MS measurement but also needs to cause α-cleavage during the ionization process. Typical examples of such a system include: a GC-MS/MS including a gas chromatograph coupled with a tandem quadrupole mass spectrometer (also called a triple quadrupole mass spectrometer) having an EI ion source; a GC-TOF/MS capable an MS/MS measurement similar to the GC-MS/MS; an LC-MS/MS capable of causing α-cleavage by in-source collision-induced dissociation; and an ion-trap LC-MS/MS capable of an $MS^n$ measurement.

In the compound-analyzing method, the compound analyzer and the computer-readable medium recording a compound-analyzing program according to the present invention, it is possible to comprehensively detect cathinone-based compounds listed in Non Patent Literature 2 by providing, as the choices of the first through third functional groups, at least the functional groups (substituent groups) disclosed in the same literature.

Specifically, the third functional group has at least nine choices: one of the eight substituents (methyl group, ethyl group, methoxy group, methylenedioxy group, fluorine atom, chlorine atom, bromine atom and iodine atom) or no functional group bonded (i.e. a hydrogen atom is bonded). The second functional group has at least three choices: one of the two substituents (methyl group and ethyl group) or no functional group bonded (i.e. a hydrogen atom is bonded). The first functional group has seven choices: one of the six substituents (methylamino group, ethylamino group, dimethylamino group, diethylamino group, methyl-ethyl-amino group and 1-pyrrolidinyl group) or no functional group bonded (i.e. an amino group is bonded).

In the compound-analyzing method according to the present invention, when a compound in a sample introduced in the mass spectrometer is ionized, a molecular ion is fragmented into ions, which are selected as precursor ions for MS/MS measurements. Specifically, when a cathinone-based compound having cathinone (i.e. 2-amino-1-phenyl-propane-1-one) as its basic skeleton is ionized by an EI method, α-cleavage occurs during the ionization, whereby the compound is split into a benzoyl part (which includes carbonyl group and benzene ring) and an amine part, and the two parts are individually ionized.

The benzoyl part thus produced contains only the third functional group. Therefore, when an MRM (multiple reaction monitoring) measurement in which the benzoyl part which contains the third functional group is selected as the precursor ion and a benzene part which also contains the third functional group is selected as the product ion is performed under various measurement conditions in which a plurality of MRM transitions corresponding to possible values of the mass of the third functional group are specified, an ion derived from the original compound is detected under a specific MRM transition corresponding to the kind of the third functional group contained in both the benzoyl part and the benzene part, while no ion is detected under the other MRM transitions. Therefore, for example, it is possible to estimate the kind of the third functional group by creating a mass chromatogram for each MRM transition and determining which chromatogram has a peak. By the present method, compounds having phenethylamine skeletons will not be detected under any of those MRM transitions. Therefore, it is possible to distinguish between cathinone-based compounds and phenethylamine-based compounds. Such a distinction is difficult to make if conventional methods are used.

On the other hand, in the second product-ion scan measurement, ions derived from the benzoyl parts which respectively contain the nine kinds of functional groups having different mass-to-charge ratios are individually selected as a precursor ion for the product-ion scan measurement. When a mass spectrum (product-ion spectrum) is created for each precursor ion, a different mass spectrum pattern appears depending on the kind of functional group. From this pattern, the kind of the third functional group can be estimated. Some functional groups produces positional isomers which have the same functional group bonded at different sites and hence show distinctly unique mass-spectrum patterns. In such a case, not only the kind of the third functional group but also its bonding site can be estimated.

Both the MRM measurement and the second product-ion scan measurement are used for estimating the kinds of the third functional group. Therefore, theoretically, performing only one of the two measurements should be sufficient to achieve the goal. However, in the product-ion scan measurement for the benzoyl part, the detection sensitivity of the product ion is not usually very high. Therefore, if the amount of the target compound is extremely small, it may be difficult to determine the mass-spectrum pattern. Meanwhile, if the MRM measurement, which is capable of detecting ions with comparatively high sensitivity, is solely performed, positional isomers cannot be identified, although the kind of the third functional group can be estimated. Accordingly, it is preferable to perform both the MRM measurement and the second product-ion scan measurement and combine the thereby obtained results.

The amine part, which is the other part produced by the α-cleavage, contains two functional groups. Within the scope of the description of Non Patent Literature 2, there are seven choices for the first functional group and three choices for the second functional group, thus making a total of 21 different combinations. However, if the sum of the mass-to-charge ratios of the two functional groups is considered, the number of choices is reduced to ten. Accordingly, in the first product-ion scan measurement, ions derived from amine parts which respectively contain the ten combinations of functional groups which differ from each other in the sum of the mass-to-charge ratios of the two functional groups are individually selected as a precursor ion for the product-ion scan measurement. When a mass spectrum (product-ion spectrum) is created for each precursor ion, a different mass-spectrum pattern appears depending on the kinds of functional groups. From this pattern, the kinds of the first and second functional groups can be estimated.

In the measurement execution step of the compound-analyzing method according to the present invention which is realized by the compound analyzer according to the present invention, two or three kinds of MS/MS measurements which have been previously determined in the previously described way are performed on a sample containing a compound which has been separated, for example, by a chromatograph. As noted earlier, it is preferable to perform the three kinds of MS/MS measurements. If a cathinone-based target compound is contained in the sample, a peak appears at the same retention time in three kinds of mass chromatograms, i.e. a mass chromatogram obtained corresponding to one MRM transition in the MRM measurement, a total ion chromatogram obtained corresponding to one precursor ion in the second product-ion scan measurement, and a total ion chromatogram obtained corresponding to one precursor ion in the first product-ion scan measurement. Accordingly, in the compound presence checking step, it is determined whether or not a peak exists at the same retention time on the aforementioned plurality of chromatograms. If such a peak is detected, it is determined that a cathinone-based compound is most likely to exist. Conversely, if there is no peak appearing at the same retention time, it means that at least one of the functional groups is absent, so that it is determined that the detected compound is not a cathinone-based compound.

When the detected compound is judged to be a probable cathinone-based compound, the structure estimation step is performed, in which the kind of the third functional group is estimated based on which of the MRM transitions in the MRM measurement has produced the detected peak and/or based on the peak pattern of the mass spectrum obtained by the second product-ion scan measurement. Furthermore, the kinds of the first and second functional groups are estimated based on the peak pattern of the mass spectrum obtained by the first product-scan measurement. By combining the results of these estimations, the chemical structure of the cathinone-based compound whose presence has been confirmed is estimated.

With the compound-analyzing method according to the present invention, it is possible to comprehensively detect a large number of cathinone-based compounds having different combinations of the three kinds of functional groups and estimate the structure of those compounds. Meanwhile, for some kinds of cathinone-based compounds, mass spectra have already been contained in existing compound databases. For such compounds, a database search may provide highly reliable results. In such a case, using the result of database search should be more advantageous for efficient analysis. Using a database search also enables an identification and/or structural analysis of a compound other than the cathinone-based compounds.

Accordingly, in one preferable mode of the compound-analyzing method according to the present invention:

the measurement execution step includes repeatedly performing a normal scan measurement which is a non-MS/MS measurement on ions derived from the sample along with the two or three kinds of MS/MS measurements;

a database-using compound identification step is additionally provided, in which a compound is identified by comparing a mass spectrum created based on data obtained by the normal scan measurement with a compound database; and the structure estimation in the structure estimation step is performed on a compound which remains unidentified after the database-using compound identification step.

For example, when a tandem quadrupole mass spectrometer is used, the "normal scan measurement which is a non-MS/MS measurement" is a scan measurement in which a mass scan is performed by either the front-stage or rear-stage quadrupole mass filter without introducing a collision-induced dissociation gas into the collision cell.

By the aforementioned preferable mode of the compound-analyzing method, at least some of the compounds registered in the compound database can be identified by the database search based on mass spectra, so that the identification and/or structural estimation of cathinone-based compounds can be efficiently performed. Compounds which are not cathinone-based compounds can also be identified if they are registered in the database.

Advantageous Effects of the Invention

With the compound-analyzing method, the compound analyzer and the computer-readable medium recording a compound-analyzing program according to the present invention, it is possible to comprehensively detect cathinone-based compounds subject to a comprehensive regulation and estimate their chemical structures using comparatively inexpensive apparatuses, such as a gas chromatograph-tandem quadrupole mass spectrometer, even if there are no standard samples available and there is no existing database prepared for the comparison of mass spectra or other information. Apparatuses used for the compound-analyzing method according to the present invention can be easily obtained. Furthermore, those apparatuses are conveniently designed to help users easily perform various settings and operations for the measurement. Therefore, an accurate analysis can be performed by not only researchers in limited areas but also by a wide range of users in various organizations, institutions, etc.

BRIEF DESCRIPTION OF DRAWINGS

FIG. 3 shows the chemical structure of a cathinone-based compound which is the target of the structural estimation.

FIG. 4 illustrates fragments to be detected by the MRM measurement.

FIG. 5 shows the correspondence relationship between the MRM transition in the MRM measurement and the kind of functional group R3 which is the target of estimation.

FIGS. 6A-6C show examples of cathinone-based compounds respectively detected for various MRM transitions as well as actually measured mass chromatograms.

FIGS. 7A-7C show examples of cathinone-based compounds respectively detected for various MRM transitions as well as actually measured mass chromatograms.

FIG. 8 shows examples of a cathinone-based compound and a phenethylamine-based compound as well as actually measured mass chromatograms.

FIGS. 11A-11C show examples of cathinone-based compounds respectively detected for various mass-to-charge ratios of the precursor ion in the first product-ion measurement as well as actually measured mass spectra.

FIGS. 12A and 12B show examples of cathinone-based compounds respectively detected for various mass-to-charge ratios of the precursor ion in the first product-ion measurement as well as actually measured mass spectra.

FIGS. 13A-13C show examples of cathinone-based compounds respectively detected for various mass-to-charge ratios of the precursor ion in the first product-ion measurement as well as actually measured mass spectra.

FIGS. 16A-16C show examples of cathinone-based compounds respectively detected for various mass-to-charge ratios of the precursor ion in the second product-ion measurement as well as actually measured mass spectra.

FIG. 17 shows examples of cathinone-based compounds detected for one mass-to-charge ratio of the precursor ion in the second product-ion scan measurement as well as actually measured mass spectra.

FIGS. 18A and 18B show examples of cathinone-based compounds respectively detected for various mass-to-charge ratios of the precursor ion in the second product-ion measurement as well as actually measured mass spectra.

DESCRIPTION OF EMBODIMENTS

Figure 1:
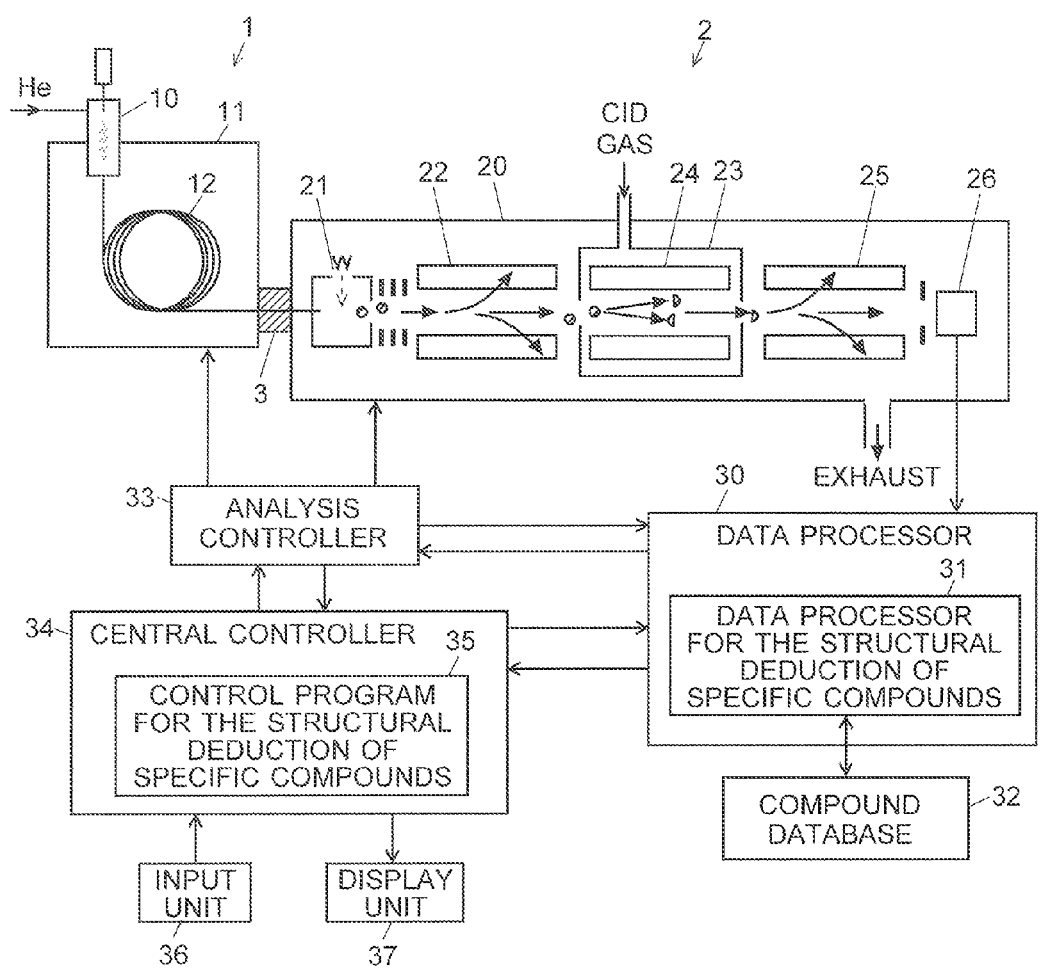
FIG. 1 is a schematic configuration diagram of one embodiment of the compound analyzer for carrying out the compound-analyzing method according to the present invention.

One embodiment of the compound analyzer for carrying out the compound-analyzing method according to the present invention is hereinafter described with reference to the attached drawings. FIG. 1 is a schematic configuration diagram of the compound analyzer according to the present embodiment.

As shown in FIG. 1, the present compound analyzer is a GC-MS/MS system including a GC unit 1 and an MS/MS unit 2. The GC unit 1 has a sample vaporization chamber 10 for vaporizing a trace amount of liquid sample, a column 12 for separating the components of the sample in the temporal direction, and a column oven 11 for controlling the temperature of the column 12. The MS/MS unit 2 has an analyzing chamber 20 evacuated by a vacuum pump (which is not shown). This chamber 20 contains an ion source 21 for ionizing a sample which is the measurement target by an electron ionization (EI) method, a front-stage quadrupole mass filter 22 and a rear-stage quadrupole mass filter 25 each of which consists of four rod electrodes, a collusion cell 23 in which a multi-pole ion guide 24 is contained, and a detector 26 for detecting ions and producing detection signals corresponding to the amount of ions. An interface unit 3, which performs a temperature control for smoothly introducing a sample gas which contains components eluted from the column 12 into the ion source 21, is provided between the GC unit 1 and the MS/MS unit 2.

An analysis controller 33 has the function of controlling the operation of each of the GC unit 1 and the MS/MS unit 2 under the command of a central controller 34. The central controller 34, which has an input unit 36 and a display unit 37 connected, is responsible for providing a user interface through these units and for conducting a general control of the entire system. The central controller 34 includes a storage device, in which a control program 35 for the structural estimation of specific compounds is stored. This program performs a characteristic control for comprehensive detection and structural estimation of specific compounds. According to this program 35, the CPU and other elements control each section of the system through the analysis controller 33 so as to execute measurements and data processing necessary for comprehensively detecting specific compounds, such as cathinone-based compounds. During this process, the detection signals (ion intensity signals) produced by the detector 26 are sent to the data processor 30, which includes a data processor 31 for the structural estimation of specific compounds. This data processor 31 performs data processing using the information stored in a compound database 32, so as to comprehensively detect specific compounds contained in the sample as well as to estimate their structures.

The central controller 34 and the data processor 30 can be embodied by using a personal computer as hardware and executing a dedicated controlling and processing software program installed in that computer. This controlling and processing software program corresponds to the component-analyzing program to be recorded in a computer-readable medium according to the present invention. In this case, a keyboard and a pointing device (e.g. mouse) serve as the input unit 36, and a display monitor serves as the display unit 37.

The basic measurement operation in the compound analyzer of the present embodiment is hereinafter schematically described.

When a trace amount of sample solution is dropped into the sample vaporization chamber 10, the sample solution quickly turns into vapor. The various compounds contained in the vaporized sample are carried into the column 12 by a carrier gas (e.g. helium). The column 12 is heated by the column oven 11, whose temperature is increased according to a preset temperature profile. While passing through this column 12, the compounds in the sample are respectively delayed by different amounts of time before reaching the exit of the column 12. The sample gas exiting from the column 12 is introduced through the interface unit 3 into the ion source 21. The ion source 21 has a filament for generating thermions. Each compound in the sample gas comes in contact with the thermions and turns into ions. In this process, one or more bonds of the ion derived from the compounds is cut (i.e. a fragmentation occurs), whereby various kinds of fragment ions are produced from one compound.

Under the control of the analysis controller 33, voltages which allow an ion having a specific mass-to-charge ratio to pass through are applied to the rod electrodes of the front-stage quadrupole mass filter 22 as well as those of the rear-stage quadrupole mass filter 25. Accordingly, only an ion having a specific mass-to-charge ratio among the various ions derived from the compounds passes through the front-stage quadrupole mass filter 22, to be introduced into the collision cell 23. The collision cell 23 is filled with an externally supplied collision-induced dissociation (CID) gas. The ion introduced into the collision cell 23 comes in contact with this gas and becomes dissociated.

The various kinds of product ions produced by this dissociation are introduced into the rear-stage quadrupole mass filter 25 while being focused by the ion guide 24. A product ion having a specific mass-to-charge ratio passes through the rear-stage quadrupole mass filter 25 and reaches the detector 26. The detection signal produced by the detector 26 is sent to the data processor 30. The data processor 30 creates mass spectra, mass chromatograms and other forms of information. It also performs other processes, such as the compound structure estimation process which will be described later.

Similar to commonly used GC-MS/MS systems, the system of the present embodiment is provided with the MRM measurement, product-ion scan measurement, precursor-ion scan measurement and neutral-loss scan measurement as the MS/MS measurement modes in the MS/MS unit 2. Normal measurements which do not include dissociation of ions within the collision cell 23 are also provided, such as a Q1 scan measurement, Q3 scan measurement, Q1-SIM measurement and Q3-SIM measurement. In the comprehensive compound structure estimation process which will be hereinafter described, the MRM measurement and the product-ion scan measurement are employed as MS/MS measurements, while the Q3 scan measurement is employed as a normal mass spectrometric measurement.

Figure 2:
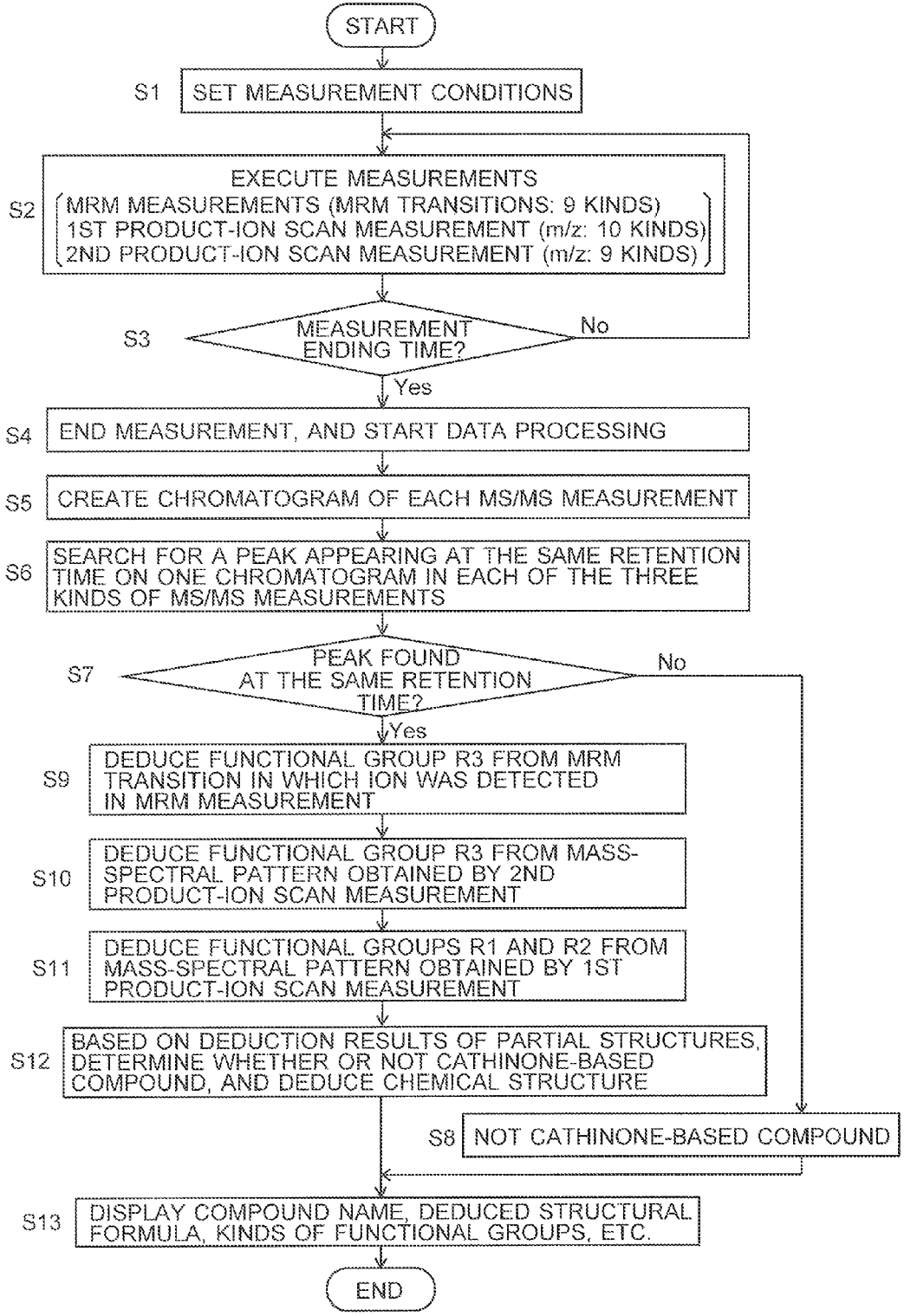
FIG. 2 is a flowchart showing the process steps of estimating the structure of a cathinone-based compound in the compound analyzer of the present embodiment.

The process of comprehensively detecting cathinone-based compounds and estimating their structures by the compound analyzer of the present embodiment is hereinafter described in detail. FIG. 2 is a flowchart showing the steps of this process.

As already noted, cathinone-based compounds having 2-amino-1-phenyl-propane-1-one (i.e. cathinone) as their basic skeleton generally have a chemical structure as shown in FIG. 3. In this basic skeleton, an amino group including a functional group R1 can be bonded to the second carbon position, a functional group R2 can be bonded to the third carbon position, and a functional group R3 can be bonded to the benzene ring. The Notice of Enforcement in Non Patent Literature 2 shows the kinds of functional groups R1, R2 and R3 that can be found in the compounds categorized as the scheduled drugs. Accordingly, to comprehensively detect those cathinone-based compounds and estimate their structures so as to identify the compounds, it is necessary to determine the kinds of three functional groups R1, R2 and R3.

As is commonly known, when a cathinone-based compound is ionized by an EI method, α-cleavage occurs, whereby the bond between the first and second carbons of the basic skeleton is cut. By this α-cleavage, the compound is divided into two parts: the benzoyl part and the amine part. The benzoyl part contains only one functional group, R3, among the three functional groups R1, R2 and R3, while the amine part contains the other two functional groups, R2 and R3. Based on this fact, in the compound analyzer of the present embodiment, the kinds of three functional groups are determined by performing MS/MS measurements in which ions that can be produced by α-cleavage are selected as precursor ions. Specifically, the following three kinds of MS/MS measurements are performed.

(1) First MS/MS Measurement: MRM Measurement

As shown in FIG. 4, the benzoyl part produced by α-cleavage in the ionization process contains only the functional group R3. When a collision-induced dissociation is performed with the benzoyl part as the target, a benzene part from which the carbonyl group is dissociated with the functional group R3 left behind is observed. In this case, both the benzoyl part and the benzene part include the functional group R3, and the mass-to-charge ratios of both the benzoyl part and the benzene part change depending on the kind of functional group R3. Accordingly, as the first MS/MS measurement, an MRM measurement is performed with the benzoyl part selected as the precursor ion and the benzene part selected as the product ion while the MRM transition is set corresponding to each of the masses of the nine kinds of functional group R3 that can be bonded to the benzene ring of the benzene part.

FIG. 5 shows the relationship between the MRM transition and the kind of functional group R3 in this MRM measurement. The shown relationship suggests that, if an ion is observed in one of the nine patterns of MRM transitions, the functional group corresponding to that MRM transition is most likely to be the functional group R3.

(2) Second MS/MS Measurement: First Product-Ion Scan Measurement

Figures 9, 10:
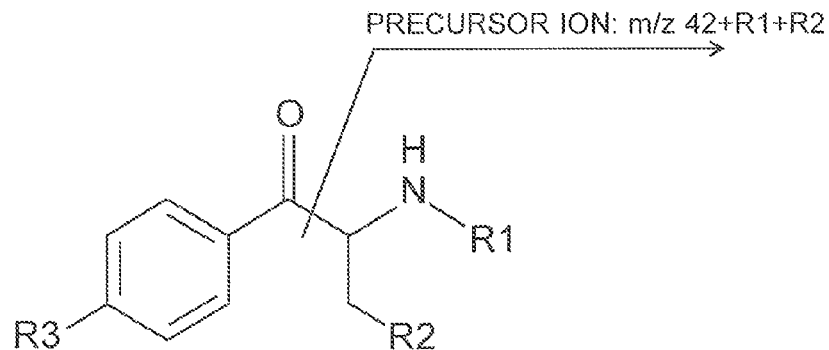
FIG. 9 illustrates a fragment to be detected by the first product-ion scan measurement.
FIG. 10 shows the correspondence relationship between the mass-to-charge ratio of the precursor ion selected in the first product-ion scan measurement and the functional groups R1 and R2 which are the target of estimation.

The amine part produced by α-cleavage includes functional groups R1 and R2. The mass of the amine part changes depending on the combination of the functional groups R1 and R2. There are only ten possible values of the sum of the masses of the functional groups R1 and R2. This means that the amine part has structural isomers which have the same mass but different functional groups R1 and R2. The difference in the structure causes a different mode of fragmentation in the collision-induced dissociation. A difference in the mode of fragmentation naturally leads to a difference in the peak pattern, i.e. the combination of the peaks which occur in the mass spectrum of the product ions. Accordingly, as the second MS/MS measurement, a product-ion scan measurement is performed in which each of the ten possible values of the mass-to-charge ratio which changes depending on the combination of the functional groups R1 and R2 in the amine part produced by α-cleavage is selected as the precursor ion. FIG. 10 shows the relationship between the mass-to-charge ratio of the precursor ion and the functional groups R1 and R2 in the second MS/MS measurement.

(3) Third MS/MS Measurement: Second Product-Ion Scan Measurement

Figures 14, 15:
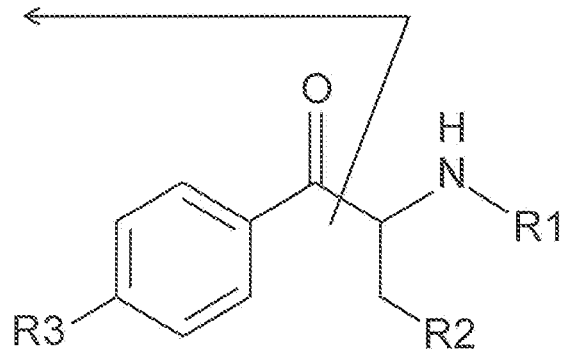
FIG. 14 illustrates a fragment to be detected by the second product-ion scan measurement.
FIG. 15 shows the correspondence relationship between the mass-to-charge ratio of the precursor ion selected in the second product-ion scan measurement and the kind of functional group R3 which is the target of estimation.

Although the kind of functional group R3 can be estimated by the previously described MRM measurement, the result obtained by the MRM measurement provides no information usable for estimating the bonding position of the functional group R3 on the benzene ring. To obtain such information, the peak pattern of the product-ion spectrum is useful. Accordingly, as the third MS/MS measurement, a product-ion scan measurement is performed in which each of the nine possible values of the mass-to-charge ratio which changes depending on the kind of functional group R3 in the benzoyl part produced by α-cleavage is selected as the precursor ion. FIG. 15 shows the relationship between the mass-to-charge ratio of the precursor ion and the functional group R3 in the third MS/MS measurement.

The measurement conditions (the measurement mode, the mass-to-charge ratios of the targets to be detected, etc.) of the three previously described kinds of MS/MS measurements are determined beforehand. Therefore, those measurement conditions can be previously stored in the control program 35 for the structural estimation of specific compounds.

Before simultaneous detection and structural estimation of cathinone-based compounds in a sample is performed, the measurement operator sets the measurement conditions through the input unit 36 (Step S1). Since the basic measurement conditions of the MS/MS measurements are previously determined, the operator only needs to set other measurement conditions as needed, such as the GC separation conditions, the scan rate in the scan measurement, and the collision energy. The task of manually setting those measurement conditions can be omitted by applying default values to all the parameters or by using a given method file.

When the measurement is initiated by a command of the measurement operator, the analysis controller 33 controls the GC unit 1 and the MS/MS unit 2 based on the instructions from the central controller 34 to repeatedly perform the MRM measurement including the nine kinds of MRM transitions (see FIG. 5), the first product-ion scan measurement for the ten values of the mass-to-charge ratio of the precursor ion (see FIG. 10) and the second product-ion scan measurement including the nine values of the mass-to-charge ratio of the precursor ion (see FIG. 15), from the measurement starting time to the measurement ending time, as well as to collect data for each measurement (Step S2). The data obtained by each measurement are stored in the memory in the data processor 30. When the measurement ending time is reached ("Yes" in Step S3), the measurement is discontinued, and subsequently, the data processor 31 for the structural estimation of specific compounds performs data processing (Step S4).

In the data processor 31 for the structural estimation of specific compounds, initially, a mass chromatogram is created for each of the MRM transitions of the MRM measurement, and furthermore, a total ion chromatogram formed by accumulating the product-ion intensity is created for each of the precursor ions selected in the first product-ion scan measurement and the second product-ion scan measurement (Step S5). Then, each of these chromatograms is subjected to a peak-detecting process, and for each detected peak, it is determined whether or not the peak in question is present at the same retention time on three chromatograms as follows: one of the nine mass chromatograms obtained by the MRM measurement, one of the ten total ion chromatograms obtained by the first product-ion scan measurement, and one of the nine total ion chromatograms obtained by the second product-ion scan measurement (Step S6).

If there is no peak found at the same retention time on the three chromatograms, it means that the compound located at that retention time does not completely have the partial structures which should be found in any cathinone-based compound subject to the comprehensive regulation. Therefore, if the presence of a common peak has not been confirmed at the same retention time ("No" in Step S7), it is determined that the detected compound is not any of the cathinone-based compounds of interest (Step S8).

If the presence of a common peak has been confirmed at the same retention time ("Yes" in Step S7), the detected compound is most likely to be a cathinone-based compound of interest. Accordingly, the kind of functional group R3 is estimated from the MRM transition in which the common peak was observed among the nine mass chromatograms obtained by the MRM measurement (Step S9). Next, the kinds of functional groups R1 and R2 are estimated from the peak pattern of the mass spectrum corresponding to the mass-to-charge ratio of the precursor ion at which the common peak was observed among the ten mass spectra obtained by the first product-ion scan measurement (Step S10). Furthermore, the kind of functional group R3 is estimated from the peak pattern of the mass spectrum corresponding to the mass-to-charge ratio of the precursor ion at which the common peak was observed among the nine mass spectra obtained by the second product-ion scan measurement (Step S11).

Based on the estimated kinds of functional groups R1, R2 and R3, the bonding position of the functional group R3 as well as other information, a final judgment is made as to whether or not the compound corresponding to the peak detected in Step S7 is a cathinone-based compound, and if the detected compound is judged to be a cathinone-based compound, its chemical structure is estimated (Step S12). Eventually, the obtained result is presented to the measurement operator on the display unit 37; specifically, when the compound is a cathinone-based compound, an analysis result is displayed including the estimated structural formula, the kinds of functional groups and other information, or when the compound is not a cathinone-based compound, a statement of this fact is displayed (Step S13). When the detected compound has been found to be a known compound, it is preferable to additionally show the compound name and other items of known information.

In the previously described process, the compound database 32 is not used for the structural estimation of the compound in the sample. However, if the detected compound is a known kind of cathinone-based compound whose mass spectrum is contained in the compound database 32, using a simple database search as before may possibly be more efficient in identifying the compound.

Accordingly, the process steps may be modified as follows: Along with the previously described MRM measurement and the product-ion scan measurements, a normal scan measurement (e.g. Q3 scan measurement) is repeatedly performed to sequentially obtain mass spectra. The first stage of the compound identification process is performed by detecting a peak on a total ion chromatogram created from the data obtained through the normal scan measurement and then comparing the pattern of the mass spectrum at the detected peak with those of the mass spectra of the cathinone-based compounds contained in the compound database 32. When a compound whose mass-spectrum pattern matches that of the detected compound is found in the database, the detected compound is most likely to be a cathinone-based compound. However, as already explained, it should be noted that, even if the search result is positive for a cathinone-based compound, the compound may actually be a phenethylamine-based compound which is difficult to be distinguished from a cathinone-based compound. In such a case, the result of the MRM measurement can be used to determine whether the detected compound is a phenethylamine-based compound or a cathinone-based compound.

After the first stage of the compound identification process, the previously described structural estimation processes from Step S5 through subsequent steps are performed to estimate the structure of cathinone-based compounds which have not been identified by the first stage of the compound identification process. The use of such a two-stage process improves the identification efficiency of the cathinone-based compounds. Additionally, if non-cathinone-based compounds are also contained beforehand in the compound database 32, various drugs and/or poisons other than cathinone-based compounds can be identified and their chemical structures can be determined.

EXAMPLES

Examples of the measurements by the cathinone-based compound analyzer of the previously described embodiment are hereinafter described in order to demonstrate that the technique applied in the compound analyzer is effective for comprehensive detection and structural analysis of cathinone-based compounds.

The devices used in the measurements and the analysis conditions are as follows:

GC-MS/MS: GCMS-TQ8030, manufactured by Shimadzu Corporation

Column: Rxi-5Sil MS (30 m in length, 0.25 mm in inner diameter, and df=0.25 μm), manufactured by Restek Corporation Temperature of the vaporization chamber in the GC unit: 260° C.

Temperature of the column oven in the GC unit: 60° C. (2 min.) 320° C. (10 min.), with a temperature-raising rate of 10° C./min Carrier-gas control in the GC unit: a constant linear velocity of 45.6 cm/sec Interface temperature of the MS unit: 280° C.

Ion source temperature of the MS unit: 200° C.

Measurement mode in the MS unit: Q3 scan/MRM/product-ion scan

Collision gas: Ar (200 KPa)

FIGS. 6A-7C show measured examples of mass chromatograms obtained by MRM measurements in which various cathinone-based compounds differing from each other in the kind of functional group R3 in the benzoyl part produced by α-cleavage were subjected to the measurement with the previously described MRM transitions. FIG. 6A shows the results of measurements performed on buphedrone and pentedrone, both having hydrogen (H) as the functional group R3, with an MRM transition of m/z: 105>77. FIG. 6B shows the results of measurements performed on 4-methylmethcathinone and 4-methylbuphedrone, both having methyl (CH3) as the functional group R3, with an MRM transition of m/z: 119>91. FIG. 6C shows the results of measurements performed on 4-methoxyethcathinone and 4-methoxymethcathinone, both having methoxy (OCH3) as the functional group R3, with an MRM transition of m/z: 135>107. FIG. 7A shows the results of measurements performed on 4-ethylmethcathinone and 3,4-dimethylmethcathinone, both having ethyl (CH2CH3) as the functional group R3, with an MRM transition of m/z: 133>105. FIG. 7B shows the results of measurements performed on 2-fluoromethcathinone and 4-fluoromethcathinone, both having fluorine (F) as the functional group R3, with an MRM transition of m/z: 123>95. FIG. 7C shows the results of measurements performed on methylone and bk-BDB, both having methylenedioxy (OCH2O) as the functional group R3, with an MRM transition of m/z: 149>121.

FIGS. 6A-7C demonstrate that, regardless of the kinds of functional groups R1 and R2 in the amine part, a peak is always observed on a chromatogram obtained in the MRM transition corresponding to the kind of functional group R3, which indicates the detection of the corresponding compound. Thus, the kind of functional group R3 can be determined by finding the MRM transition in which a chromatogram peak is observed.

FIG. 8 shows measured examples of mass chromatograms obtained by an MRM measurement of 4-methoxymethcathinone having the cathinone skeleton and 4-methoxymethamphetamine having a structure extremely similar to that of 4-methoxymethcathinone except for its phenethylamine skeleton, with an MRM transition of m/z: 135>107. In the case of 4-methoxymethcathinone, a chromatogram peak is observed since it has the cathinone skeleton. By contrast, in the case of 4-methoxymethamphetamine having the phenethylamine skeleton, no chromatogram peak is observed since the compound has no carbonyl group. If mass spectra obtained by a conventional EI-scan process are used, it is difficult to distinguish between 4-methoxymethcathinone and 4-methoxymethamphetamine. By the present method, it is possible to easily distinguish between cathinone-based compounds and phenethylamine-based compounds by determining whether or not a peak is present on a mass chromatogram corresponding to a predetermined MRM transition.

Even if an analogue compound having a functional group R3 other than the nine currently considered kinds is circulated as an illicit drug in the future, the analogue compound having the new functional group R3 can be detected by adding another MRM transition to the MRM measurement taking into account the mass of that functional group R3.

FIGS. 11A-13C show measured examples of mass spectra (product-ion spectra) obtained by performing the first product-ion scan measurement in the previously described manner on various cathinone-based compounds having different combinations of the functional groups R1 and R2 in the amine part produced by α-cleavage.

FIG. 11A shows the result of a product-ion scan measurement performed on 4-ethylcathinone with a mass-to-charge ratio of m/z: 44 selected as the precursor ion. FIG. 11B shows the results of product-ion scan measurements performed on bk-BDB and methcathinone with a mass-to-charge ratio of m/z: 58 selected as the precursor ion. FIG. 11C shows the results of product-ion scan measurements performed on desmethylpentylone, buphedrone, ethcathinone and 4-ethyl-N, N-dimethylcathinone with a mass-to-charge ratio of m/z: 72 selected as the precursor ion.

FIG. 12A shows the results of product-ion scan measurements performed on pentedrone, N-ethylbuphedrone and bk-MDDMA with a mass-to-charge ratio of m/z: 86 selected as the precursor ion. FIG. 12B shows the results of product-ion scan measurements performed on N-ethylpentedrone and N,N-dimethylpentylone with a mass-to-charge ratio of m/z: 100 selected as the precursor ion.

FIG. 13A shows the result of a product-ion scan measurement performed on α-PPP with a mass-to-charge ratio of m/z: 98 selected as the precursor ion. FIG. 13B shows the result of a product-ion scan measurement performed on α-PBP with a mass-to-charge ratio of m/z: 112 selected as the precursor ion. FIG. 13C shows the result of a product-ion scan measurement performed on α-PVP with a mass-to-charge ratio of m/z: 126 selected as the precursor ion.

For example, the amine parts respectively produced by α-cleavage of the four kinds of compounds shown in FIG. 11C are structural isomers having the same mass. However, the patterns of their mass spectra obtained by the product-ion scan measurements are different from each other. This fact also holds true for the other mass-to-charge ratios of the precursor ion. Therefore, it is possible to estimate the kinds of functional groups R1 and R2 included in the amine part produced by α-cleavage as well as the structure of the amine part by finding the mass-to-charge ratio of the precursor ion at which ions are detected in the product-ion scan measurement and by investigating the mass-spectrum pattern of those ions.

Even if an analogue compound having a combination of functional groups R1 and R2 other than the ten currently considered combinations is circulated as an illicit drug in the future, the analogue compound having the new functional groups R1 and R2 can be detected by adding a product-ion scan measurement for another mass-to-charge ratio of the precursor ion selected taking into account the mass of the combination of those functional groups R1 and R2 and by collecting mass-spectrum information of that precursor ion.

FIGS. 16A-18B show measured examples of mass spectra (product-ion spectra) obtained by performing the second product-ion scan measurement in the previously described manner on various cathinone-based compounds having different functional groups R3 in the benzoyl part produced by α-cleavage.

FIG. 16A shows the result of a product-ion scan measurement performed on buphedrone with a mass-to-charge ratio of m/z: 105 selected as the precursor ion. FIG. 16B shows the result of a product-ion scan measurement performed on 4-methylmethcathinone with a mass-to-charge ratio of m/z: 119 selected as the precursor ion. FIG. 16C shows the result of a product-ion scan measurement performed on 4-methoxyethcathinone with a mass-to-charge ratio of m/z: 135 selected as the precursor ion.

FIG. 17 shows the results of product-ion scan measurements performed on 2-ethylmethcathinone, 3-ethylmethcathinone, 4-ethylmethcathinone and 3,4-dimethylmethcathinone with a mass-to-charge ratio of m/z: 133 selected as the precursor ion.

FIG. 18A shows the results of product-ion scan measurements performed on 2-fluoromethcathinone, 3-fluoromethcathinone and 4-fluoromethcathinone with a mass-to-charge ratio of m/z: 123 selected as the precursor ion. FIG. 18B shows the result of a product-ion scan measurement performed on methylone with a mass-to-charge ratio of m/z: 149 selected as the precursor ion.

For example, the benzoyl parts respectively produced by α-cleavage of the four kinds of compounds shown in FIG. 17 are positional isomers having the same mass. However, the patterns of their mass spectra obtained by the product-ion scan measurements are different from each other. This fact also holds true for the other mass-to-charge ratios of the precursor ion. Therefore, it is possible to estimate the kind of functional group R3 included in the benzoyl part produced by α-cleavage as well as a partial structure of the benzoyl part by finding the mass-to-charge ratio of the precursor ion at which ions are detected in the product-ion scan measurement and by investigating the mass-spectrum pattern of those ions. When the functional group R3 is fluorine or chlorine, both of which are halogens, no significant difference in the mass-spectrum pattern occurs among the positional isomers and it is difficult to distinguish between those positional isomers. However, it is possible to estimate at least the kind of functional group R3 by finding the mass-to-charge ratio of the precursor ion at which the product-ion peaks are detected.

Even if an analogue compound having a functional group R3 other than the nine currently considered kinds is circulated as an illicit drug in the future, the analogue compound having the new functional group R3 can be detected by adding a product-ion scan measurement for another mass-to-charge ratio of the precursor ion selected taking into account the mass of the functional group R3 and by collecting mass-spectrum information of that precursor ion.

The measured results described thus far verify that, with the compound analyzer according to the present invention, it is possible to comprehensively detect illicit cathinone-based drugs having cathinone as their basic skeleton and to estimate their structures from the results of measurements using a GC-MS/MS system.

It is evident that the previous embodiment is a mere example of the present invention and can be appropriately changed or modified within the spirit of the present invention.

For example, a liquid chromatograph may be used in place of the gas chromatograph used in the previous embodiment in order to separate compounds in a sample. However, it should be noted that an atmospheric pressure ionization method is generally used for the ionization of compounds in a sample liquid eluted from a column of a liquid chromatograph, and that atmospheric pressure ionization methods barely cause α-cleavage during the ionization process. To solve this problem, it is preferable to use an ion source having the function of an in-source CID so that fragment ions similar to those created by the EI method can be obtained.

REFERENCE SIGNS LIST

1 . . . GC Unit
10 . . . Sample Vaporization Chamber
11 . . . Column Oven
12 . . . Column
2 . . . MS/MS Unit
20 . . . Analyzing Chamber
21 . . . Ion Source
22 . . . Front-Stage Quadrupole Mass Filter
23 . . . Collision Cell
24 . . . Multi-Pole Ion Guide
25 . . . Rear-Stage Quadrupole Mass Filter
26 . . . Detector
3 . . . Interface Unit
30 . . . Data Processor
31 . . . Data Processor for the Structural Estimation of Specific Compounds
32 . . . Compound Database
33 . . . Analysis Controller
34 . . . Central Controller
35 . . . Control Program for the Structural Estimation of Specific Compounds
36 . . . Input Unit
37 . . . Display Unit

The invention claimed is:

1. A compound-analyzing method for detecting a cathinone-based compound having cathinone as a basic skeleton and for estimating a structure of the cathinone-based compound, using a chromatograph mass spectrometer capable of an MS/MS measurement, the compound-analyzing method comprising:
  a) a measurement execution step, in which a sample which contains or possibly contains a compound which is an analysis target is separated into components by a chromatograph and two or three kinds of MS/MS measurements are repeatedly performed on the sample, the two or three kinds of measurements including:
    a1) one or both of following two kinds of measurements: an MRM measurement, in which a benzoyl part produced by α-cleavage during an ionization process is selected as a precursor ion, a benzene part produced by dissociation of a carbonyl group from the benzoyl part is selected as a product ion, and a plurality of MRM transitions corresponding to possible values of a mass of a third functional group bonded to a benzene ring are specified as measurement conditions; and a second product-ion scan measurement performed for a benzoyl part produced by α-cleavage during an ionization process, in which each of a plurality of kinds of benzoyl parts corresponding to the possible mass values of the third functional group is selected as a precursor ion; and
    a2) a first product-ion scan measurement performed for an amine part produced by α-cleavage during an ionization process, in which each of a plurality of kinds of amine parts corresponding to possible values of a total mass of a first functional group and a second functional group respectively bonded to different sites on the amine part is selected as a precursor ion;

b) a compound presence checking step, in which a presence of a cathinone-based compound is judged by determining whether or not a common peak exists at a same retention time on chromatograms respectively corresponding to the two or three kinds of measurements, the chromatograms being created based on data respectively obtained by the MRM measurement and/or the second product-ion scan measurement as well as the first product-ion scan measurement; and c) a structure estimation step, in which a kind of the third functional group is estimated based on the data obtained by the MRM measurement and/or the second product-ion scan measurement, kinds of the first functional group and the second functional group are estimated based on the data obtained by the first product-ion scan measurement, and results of these estimations are combined to estimate a structure of a cathinone-based compound whose presence is confirmed in the compound presence checking step.

2. The compound-analyzing method according to claim 1, wherein:
the measurement execution step includes repeatedly performing a normal scan measurement which includes no dissociation of ions derived from the sample along with the two or three kinds of MS/MS measurements;
a database-using compound identification step is additionally provided, in which a compound is identified by comparing a mass spectrum created based on data obtained by the normal scan measurement with a compound database; and
the structure estimation in the structure estimation step is performed on an unknown compound which is not registered in the compound database.

3. A compound analyzer including a chromatograph mass spectrometer capable of an MS/MS measurement and being configured to detect a cathinone-based compound having cathinone as a basic skeleton and to estimate a structure of the cathinone-based compound, the compound analyzer further comprising:

a) an analysis controller for making the chromatograph mass spectrometer operate so as to separate a sample which contains or possibly contains a compound which is an analysis target into compounds by a chromatograph and to repeatedly perform two or three kinds of MS/MS measurements on the sample, the two or three kinds of MS/MS measurements including:
a1) one or both of following two kinds of measurements: an MRM measurement, in which a benzoyl part produced by α-cleavage during an ionization process is selected as a precursor ion, a benzene part produced by dissociation of a carbonyl group from the benzoyl part is selected as a product ion, and a plurality of MRM transitions corresponding to possible values of a mass of a third functional group bonded to a benzene ring are specified as measurement conditions; and a second product-ion scan measurement performed for a benzoyl part produced by α-cleavage during an ionization process, in which each of a plurality of kinds of benzoyl parts corresponding to the possible mass values of the third functional group is selected as a precursor ion; and
a2) a first product-ion scan measurement performed for an amine part produced by α-cleavage during an ionization process, in which each of a plurality of kinds of amine parts corresponding to possible values of a total mass of a first functional group and a second functional group respectively bonded to different sites on the amine part is selected as a precursor ion;

b) a compound presence checker for collecting data respectively obtained by the MRM measurement and/or the second product-ion scan measurement as well as the first product-ion scan measurement, for creating chromatograms corresponding to the two or three kinds of MS/MS measurements based on the data, and for judging a presence of a cathinone-based compound by determining whether or not a common peak exists at a same retention time on the chromatograms; and c) a structure estimator for estimating a kind of the third functional group based on the data obtained by the MRM measurement and/or the second product-ion scan measurement, for estimating kinds of the first functional group and the second functional group based on the data obtained by the first product-ion scan measurement, and for combining results of these estimations to estimate a structure of a cathinone-based compound whose presence is confirmed by the compound presence checker.

4. A computer-readable medium recording a computer program, the compound-analyzing program being configured to be executed on a computer so as to control an operation of a chromatograph mass spectrometer capable of an MS/MS measurement as well as to collect and process data obtained by the chromatograph mass spectrometer in order to detect a cathinone-based compound having cathinone as a basic skeleton and estimate a structure of the cathinone-based compound, the compound-analyzing program comprising:

a) an analysis control functional part for making the chromatograph mass spectrometer operate so as to separate a sample which contains or possibly contains a compound which is an analysis target into compounds by a chromatograph and to repeatedly perform two or three kinds of MS/MS measurements on the sample, the two or three kinds of MS/MS measurements including:
a1) one or both of following two kinds of measurements: an MRM measurement, in which a benzoyl part produced by α-cleavage during an ionization process is selected as a precursor ion, a benzene part produced by dissociation of a carbonyl group from the benzoyl part is selected as a product ion, and a plurality of MRM transitions corresponding to possible values of a mass of a third functional group bonded to a benzene ring are specified as measurement conditions; and a second product-ion scan measurement performed for a benzoyl part produced by α-cleavage during an ionization process, in which each of a plurality of kinds of benzoyl parts corresponding to the possible mass values of the third functional group is selected as a precursor ion; and
a2) a first product-ion scan measurement performed for an amine part produced by α-cleavage during an ionization process, in which each of a plurality of kinds of amine parts corresponding to possible values of a total mass of a first functional group and a second functional group respectively bonded to different sites on the amine part is selected as a precursor ion;

b) a compound presence checking functional part for creating chromatograms corresponding to the two or three kinds of MS/MS measurements based on data respectively obtained by the MRM measurement and/or the second product-ion scan measurement as well as the first product-ion scan measurement, and for judging a presence of a cathinone-based compound by determining whether or not a common peak exists at a same retention time on the chromatograms; and c) a structure estimation functional part for estimating a kind of the third functional group based on the data obtained by the MRM measurement and/or the second product-ion scan measurement, for estimating kinds of the first functional group and the second functional group based on the data obtained by the first product-ion scan measurement, and for combining results of these estimations to estimate a structure of a cathinone-based compound whose presence is confirmed by a process performed by the compound presence checking functional part.

* * * * *